(12) United States Patent
Kizer et al.

(10) Patent No.: US 10,729,814 B2
(45) Date of Patent: Aug. 4, 2020

(54) NEOCARTILAGE COMPOSITIONS AND METHODS FOR MODIFYING PROTEOGLYCAN CONTENT

(71) Applicant: ISTO Technologies, Inc., St. Louis, MO (US)

(72) Inventors: Neil Kizer, St. Louis, MO (US); Nicole M. Bergmann, St. Louis, MO (US); Gary Gage, St. Louis, MO (US); Huston Davis Adkisson, St. Louis, MO (US); Michael Maloney, St. Louis, MO (US)

(73) Assignee: Isto Technologies, Inc., St. Louis, MO (US)

( * ) Notice: Subject to any disclaimer, the term of this patent is extended or adjusted under 35 U.S.C. 154(b) by 538 days.

(21) Appl. No.: 15/501,155

(22) PCT Filed: Jul. 30, 2015

(86) PCT No.: PCT/US2015/042960
§ 371 (c)(1),
(2) Date: Feb. 1, 2017

(87) PCT Pub. No.: WO2016/019170
PCT Pub. Date: Feb. 4, 2016

(65) Prior Publication Data
US 2017/0360989 A1    Dec. 21, 2017

Related U.S. Application Data

(60) Provisional application No. 62/032,255, filed on Aug. 1, 2014.

(51) Int. Cl.
*A61L 27/38* (2006.01)
*A61L 27/36* (2006.01)
(Continued)

(52) U.S. Cl.
CPC .......... *A61L 27/3817* (2013.01); *A61K 35/32* (2013.01); *A61L 27/227* (2013.01);
(Continued)

(58) Field of Classification Search
CPC ............... A61L 27/3817; A61L 27/227; A61L 27/3695; A61L 27/3612; A61L 27/34;
(Continued)

(56) References Cited

U.S. PATENT DOCUMENTS 6,235,316 B1    5/2001   Adkisson
6,645,764 B1   11/2003   Adkisson
(Continued)

OTHER PUBLICATIONS

Adkisson, H.D. et al, In Vitro Generation of Scaffold Independent Neocartliage, Clinical Orthopaedics and Related Research, 2001, pp. S280-S294, No. 391S.
(Continued)

*Primary Examiner* — Carlos A Azpuru
(74) *Attorney, Agent, or Firm* — Polsinelli PC

(57) ABSTRACT

The present disclosure relates to cartilage repair compositions and methods for modifying the proteoglycan content of the compositions. Specifically, the methods relate to serum free, collagen free neocartilage made from chondrocytes that can be used for implants. Proteoglycans, such as aggrecan and sulfated glycosaminoglycan are used and the content modified using temperature changes.

16 Claims, 1 Drawing Sheet

(51) Int. Cl.
*A61K 35/32* (2015.01)
*C12N 5/077* (2010.01)
*A61L 27/34* (2006.01)
*A61L 27/22* (2006.01)
*C07K 14/47* (2006.01)

(52) U.S. Cl.
CPC ........... *A61L 27/34* (2013.01); *A61L 27/3612* (2013.01); *A61L 27/3695* (2013.01); *C07K 14/4725* (2013.01); *C12N 5/0655* (2013.01); *A61L 2430/06* (2013.01); *A61L 2430/40* (2013.01); *C12N 2523/00* (2013.01)

(58) Field of Classification Search
CPC . A61L 2430/06; A61L 2430/40; A61K 35/32; C07K 14/4725; C12N 5/0655; C12N 2523/00
See application file for complete search history.

(56) References Cited

U.S. PATENT DOCUMENTS

| | | | |
|---|---|---|---|
| 7,087,227 | B2 | 8/2006 | Adkisson |
| 7,273,756 | B2 | 9/2007 | Adkisson et al. |
| 8,017,394 | B2 | 9/2011 | Adkisson, IV et al. |
| 2002/0082220 | A1* | 6/2002 | Hoemann ............ A61K 31/727 514/13.6 |
| 2003/0224518 | A1* | 12/2003 | Adkisson, IV ........ A61K 35/32 435/375 |
| 2008/0081369 | A1 | 4/2008 | Adkisson, IV et al. |
| 2009/0143867 | A1 | 6/2009 | Gage et al. |
| 2012/0100185 | A1 | 4/2012 | Wen et al. |
| 2014/0193468 | A1 | 7/2014 | Tarrant et al. |

OTHER PUBLICATIONS

Australian Application 2015296246 Office Action dated Aug. 16, 2017, 5 pages.
Osman, N. et al, Combined transgenic expression of α-galactosidase and α1,2-fucosyltransferase leads to optimal reduction in the major xenoepitope Galα(1,3)Gal, PNAS, 1997, pp. 14677-14682, vol. 94.
Sandrin, M.S. et al, Transgenic Approaches for the Reduction in Expression of GALα(1,3)GAL for Xenotransplantation, Frontiers in Bioscience, 1997, pp. E1-11, No. 2.
PCT/US2015/042960 International Search Report and Written Opinion dated Oct. 29, 2015, 11 pages.
European Application 15827329.2 Extended Search Report dated Mar. 20, 2018, 7 pages.
Canadian Application 2,956,359 Office Action dated Jan. 8, 2018, 5 pages.

* cited by examiner

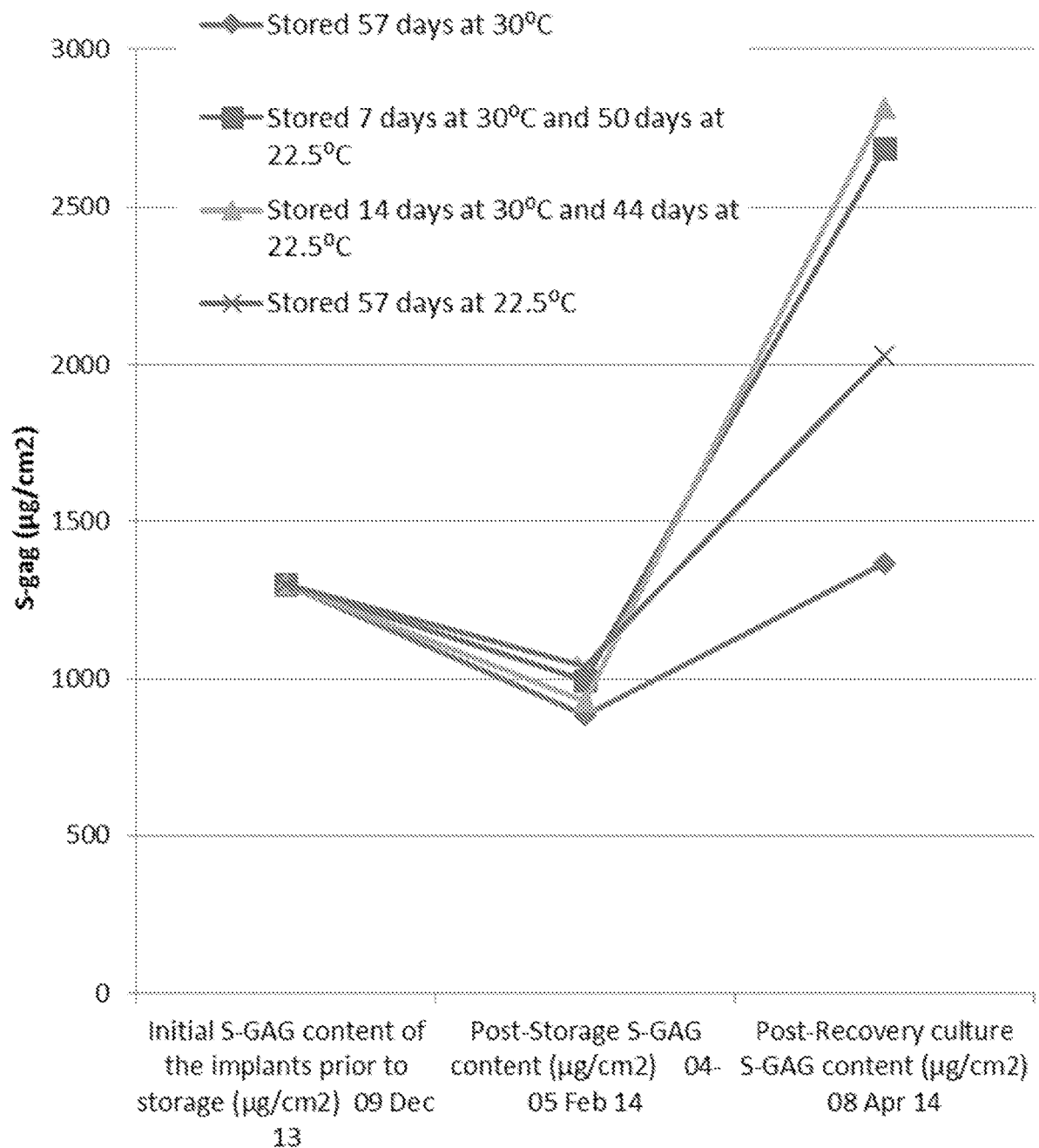

NEOCARTILAGE COMPOSITIONS AND METHODS FOR MODIFYING PROTEOGLYCAN CONTENT

FIELD OF THE INVENTION

The present disclosure relates to cartilage repair compositions and methods for modifying the proteoglycan content of the compositions.

SUMMARY OF THE INVENTION

In one aspect, the present disclosure provides a cartilage replacement composition comprising: neocartilage maintained at a temperature below physiologic temperature for a period of time sufficient for the proteoglycan content of the neocartilage to decrease relative to the proteoglycan content of the neocartilage at a physiological temperature, wherein the neocartilage at the temperature of about 30° C. or lower is capable of increasing the proteoglycan content when returned to a physiological temperature. Put another way, the proteoglycan content is capable of being increased when the neocartilage is returned to a physiological temperature.

In another aspect, the present disclosure provides a cartilage replacement composition comprising: cartilage tissue prepared ex vivo from isolated chondrocytes, the cartilage tissue maintained at a temperature below physiologic temperature for a period of time sufficient for the proteoglycan content of the cartilage tissue to decrease relative to the proteoglycan content of the cartilage tissue at a physiological temperature, wherein the cartilage tissue at the temperature of about 30° C. or lower is capable of increasing the proteoglycan content when returned to a physiological temperature. Put another way, the proteoglycan content of the cartilage tissue is capable of being increased when the cartilage tissue is returned to a physiological temperature.

Any cartilage replacement composition described herein can be characterized by any one, any set of or all the following:
  the temperature below physiologic temperature is about 30° C. or lower
  the proteoglycan content comprises aggrecan content.
  the proteoglycan content comprises sulfated glycosaminoglycan (S-GAG) content.
  an initial proteoglycan content of the neocartilage at a physiological temperature before being maintained at about 30° C. or lower, comprises an initial S-GAG content of at least about 400 or at least about 500 µg/cm2.
  the initial proteoglycan content comprises an S-GAG content of from about 800 µg/cm2 to about 2500 µg/cm2.
  the composition is substantially free of type I, III and X collagen.
  the initial proeteoglycan content of the composition indicates cartilage enriched in high molecular weight aggrecan.
  the high molecular weight aggrecan comprises at least about 80% of the initial proteoglycan content of the cartilage.
  the high molecular weight aggrecan comprises at least about 90% of the initial proteoglycan content of the cartilage.
  the physiological temperature is about 37° C.
  when the composition is maintained at the physiological temperature, the composition is further maintained under normoxic or hypoxic conditions.
  the composition restored to the physiological temperature for a period of time sufficient for the proteoglycan content of the composition to increase relative to the decreased proteoglycan content of the composition while maintained at about 30° C. or lower.
  the composition comprises articular chondrocytes obtained from a human or animal donor.
  the composition comprises articular chondrocytes obtained from a juvenile donor.
  the composition comprises articular chondrocytes obtained from a cadaver.
  the composition comprises an implant.
  the composition is maintained at a temperature of about 20-30° C.
  the composition when maintained at a temperature below physiologic temperature is enclosed in a sealed container, i.e. wherein air exposure is reduced or eliminated.
  the sealed container is selected from the group consisting of: a foil pouch, a sealed PETG tray and a glass jar.
  the storage period is at least about 1 week, at least about 2 weeks, at least about 30 days, at least about 50 days, at least about 60 days, at least about 90 days, at least about 120 days, at least about 150 days, or at least about 360 days.
  the composition is maintained in a serum-free medium before, and/or during and or after maintenance at a temperature below physiologic temperature.
  the composition is maintained in a serum-free medium in the sealed container.

In another aspect, the present disclosure provides a method for modifying the proteoglycan content of a cartilage composition for the repair of cartilage tissue, the method comprising:
  a) obtaining the cartilage composition, wherein the cartilage composition has previously been maintained at a physiological temperature and has an initial proteoglycan content;
  b) sealing the cartilage composition in a container in a serum-free medium;
  c) maintaining the cartilage composition in the sealed container at a storage temperature below physiologic temperature for a storage period of time sufficient for the proteoglycan content of the cartilage composition to decrease to a storage proteoglycan content less than the initial proteoglycan content;
  d) then removing the cartilage composition from the container and the storage temperature and returning the cartilage composition to recovery conditions comprising a serum-free medium and a physiological temperature;
  e) maintaining the cartilage composition under the recovery conditions for a period of time sufficient for the proteoglycan content of the cartilage composition to increase to a recovery proteoglycan content.
  cartilage defect of a subject.

In another aspect, the present disclosure provides a method a method for of repairing cartilage tissue of a subject, the method comprising:
  a) obtaining a cartilage composition prepared by a process comprising sealing the cartilage composition in a container in a serum-free medium, and maintaining the cartilage composition in the sealed container at a storage temperature below physiologic temperature for a storage period of time sufficient for the proteoglycan content of the cartilage composition to decrease to a storage proteoglycan content less than the initial proteoglycan content;

b) then removing the cartilage composition from the container and the storage temperature; and c) implanting the cartilage composition in a cartilage defect of the subject, wherein the implantation returns the cartilage composition to a physiological temperature;

d) maintaining the cartilage composition in the defect for a period of time sufficient for the proteoglycan content of the cartilage composition to increase to a recovery proteoglycan content of the composition.

In any of the methods, a temperature below physiologic temperature can be about 30° C. or lower. The initial, storage and recovery proteoglycan contents can each comprise aggrecan content. The initial, storage and recovery proteoglycan contents each comprise sulfated glycosaminoglycan (S-GAG) content. The initial proteoglycan content of the neocartilage at a physiological temperature before being maintained at about 30° C. or lower, can comprise an initial S-GAG content of at least about 400 or at least about 500 μg/cm2. The initial proteoglycan content can comprise an S-GAG content of from about 800 μg/cm2 to about 2500 μg/cm2. The composition can be substantially free of type I, III and X collagen. The initial proteoglycan content of the composition can indicate cartilage enriched in high molecular weight aggrecan. The high molecular weight aggrecan can comprise at least about 80% of the initial proteoglycan content of the cartilage. The high molecular weight aggrecan can comprises at least about 90% of the initial proteoglycan content of the cartilage. The physiological temperature can be about 37° C. The composition prior to step (a) can be previously maintained under normoxic or hypoxic conditions, and during recovery conditions in steps (d) and (e), the composition can be further maintained under normoxic or hypoxic conditions. The composition can comprise articular chondrocytes obtained from a human or animal donor, a juvenile donor, a deceased individual (animal or human, i.e. cadaver). The composition can comprise an implant. In step (c) the composition can be maintained at a temperature of about 20-30° C. The sealed container can be selected from the group consisting of: a foil pouch, a sealed PETG tray and a glass jar. The storage period in step (c) can be at least about 1 week, at least about 2 weeks, at least about 30 days, at least about 50 days, or at least about 60 days at least about 90 days, at least about 120 days, at least about 150 days, or at least about 360 days.

Maintaining the cartilage composition under the recovery conditions for a period of time sufficient for the proteoglycan content of the cartilage composition to increase to a recovery proteoglycan content can comprise implanting the cartilage composition in a In another aspect, the present disclosure provides a cartilage composition prepared by any of the disclosed methods.

In another aspect, the present disclosure provides a cartilage composition comprising a cartilage composition prepared ex vivo and subjected ex vivo to a storage temperature below physiologic temperature for a storage period of time sufficient for the proteoglycan content of the cartilage composition to decrease to a storage proteoglycan content less than an initial proteoglycan content, and then restored to physiologic temperature, wherein once restored to the physiologic temperature the cartilage composition provides a viable cartilage replacement material.

BRIEF DESCRIPTION OF THE DRAWINGS

FIG. 1 is a graph of proteoglycan (S-gag) content of implants over time during a recovery culture period.

DETAILED DESCRIPTION OF THE DISCLOSURE

The present disclosure provides methods for modifying the proteoglycan content of a cartilage composition for the repair of cartilage tissue, based in part on the surprising discovery that the proteoglycan content of cartilage compositions prepared ex vivo from isolated chondrocytes can be manipulated by changing the temperature of the composition. For example, the proteoglycan content can be reduced by reducing the temperature of the composition below physiological temperature, and then the proteoglycan content can be restored by restoring the temperature of the composition to physiological temperature.

As used herein, the term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig). Preferably, the subject is a human.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The terms "chondrocyte" and "chondrocytes" as used herein refer to cartilage-specific cells that give rise to normal cartilage tissue growth in vivo; these cells synthesize and deposit the supportive matrix (composed principally of collagen and proteoglycan) of cartilage.

The term "phenotype" refers to the observable characteristics at any level—physical, morphologic, biochemical or molecular—of a cell or tissue.

The term "hyaluronic acid" as used herein is interchangeable with the terms "hyaluronate", "hyaluronan" and "HA", and refers to a polysaccharide composed of repeating disaccharide units of N-acetylglucosamine and glucuronic acid. Commercial HA is commonly its sodium salt form. HA may be a natural or synthetic hyaluronate, such as sodium hyaluronate purified either from rooster combs or from bacterial fermentation.

The term "cytokine" as used herein is interchangeable with the terms "growth factor", and refers to a broad range of relatively low molecular weight, pharmacologically active proteins that are secreted by one cell for the purpose of altering either its own function(s) (autocrine effect) or those of adjacent cells (paracrine effect). Individual cytokines can have multiple biological activities. Different cytokines can also have redundant activity.

Generally, nomenclatures used in connection with, and techniques of, cell and tissue culture, molecular biology, immunology, microbiology, genetics and protein and nucleic acid chemistry and hybridization described herein are well known and commonly used in the art. The methods and techniques of the present disclosure are generally performed according to conventional methods well known in the art and as described in various general and more specific references that are cited and discussed throughout the present specification unless otherwise indicated. Any chemical, enzymatic or staining reactions, or purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also well known and commonly used in the art. Standard techniques are used for chemical syntheses, chemical analyses, pharmaceutical preparation, formulation, delivery, diagnosis and treatment of all subjects, human and animal.

A. Cartilage Compositions and Methods

Basic cell isolation, culture and expansion methods, particularly those for isolating, culturing and expanding chondrocytes, are well known in the art and commonly used. Methods for preparing cartilage compositions cartilage compositions prepared ex vivo from isolated chondrocytes, such as neocartilage and implants composed of such compositions, are as previously described in U.S. Pat. Nos. 6,645,764; 6,235,316; 7,087,227; 7,273,756; and 8,017,394, the entire disclosures of each of which are herein incorporated by reference. Unless otherwise indicated herein, methods and procedures are performed according to conventional methods well known in the art and as described for example in U.S. Pat. Nos. 6,645,764; 6,235,316; 7,087,227; 7,273,756; and 8,017,394.

The methods and systems described herein are based in part on the surprising discovery that the proteoglycan content of cartilage compositions prepared ex vivo from isolated chondrocytes can be manipulated by changing the temperature of the composition. For example, the proteoglycan content can be decreased by reducing the temperature of the composition below a physiological temperature, and then especially surprisingly, the proteoglycan content can be increased by restoring the temperature of the composition to physiological temperature. Preferably, when the temperature of the composition is reduced, the composition is maintained in a tissue medium, preferably a serum-free medium, in a sealed container, i.e. a container which reduced or eliminates exposure of the composition to air. Restoring the temperature of the composition to physiological temperature can be achieved by restoring the composition to in vitro culture conditions providing physiological temperature and normoxic or hypoxic conditions, and/or implanting the composition in vivo in a live subject, for example implanting into a cartilage defect in the subject.

Chondrocytes for preparing a cartilage composition according to the present methods, can be isolated for example from cartilage derived from a human or animal donor. An exemplary donor is an immature or juvenile donor, including a neonatal, infant, or pre-adolescent donor. A donor can be a deceased individual, including a deceased immature or juvenile donor. Chondrocytes can be avian or mammalian chondrocytes, preferably human chondrocytes. Chondrocytes can be derived from transgenic animals that have been genetically engineered to prevent immune-mediated xenograft rejection (Sandrin et al., 1995; Sandrin et al., 1996 and Osman et al., 1997). Cartilage can be obtained from any tissue containing hyaline, elastic or fibro-cartilage. Chondrocytes can be isolated by methods known in the art such as by sequential enzymatic digestion techniques (Adkisson et al., 2001).

An expansion culture for preparing the cartilage compositions can be produced for example by isolating immature chondrocytes, e.g., neonatal, infant or pre-adolescent, from donor articular cartilage and plating the dissociated cells into culture medium in a culture plate or vessel. The culture medium is preferably a substantially serum-free or serum-free expansion medium. A "chemically defined" medium is a serum-free medium, the chemical components of which are known. The culture medium is preferably a serum-free medium comprising at least one growth factor. An exemplary substantially serum-free growth media is HL-1®, a serum-free media containing insulin-transferrin-selenium-complex as its only source of protein. HL-1® is available from BioWhittaker, Walkersville, Md. Other suitable serum-free growth media will be readily apparent to those skilled in the art.

In any of the methods or for preparing any of the compositions, a suitable culture medium optionally comprises at least one growth factor can be selected for example from: Adrenomedullin (AM), Angiopoietin (Ang), Autocrine motility factor, Bone morphogenetic proteins (BMPs) including BMP-2, BMP-4 and BMP-7, Brain-derived neurotrophic factor (BDNF), Chondromodulin-I (ChM-I), Chondromodulin-II (ChM-II) Epidermal growth factor (EGF), Erythropoietin (EPO), Fibroblast growth factor (FGF), FGF-2, FGF-9, FGF-18, Glial cell line-derived neurotrophic factor (GDNF), Granulocyte colony-stimulating factor (G-CSF), Granulocyte macrophage colony-stimulating factor (GM-CSF), Growth differentiation factor-5 (GDF5), Growth differentiation factor-9 (GDF9), Healing factor, Hepatocyte growth factor (HGF), Hepatoma-derived growth factor (HDGF), Insulin-like growth factor (IGF), Keratinocyte growth factor (KGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), TGF-β1, TGF-β2, TGF-β3, Tumor necrosis factor-alpha (TNF-α), Vascular endothelial growth factor (VEGF), Wnt Signaling Pathway, placental growth factor (PGF), PDGF-bb, Pleotrophin, and SDF-1.

In any of the methods or for preparing any of the compositions, a suitable medium optionally comprises at least one culture supplement selected from the group consisting of: soluble Type II collagen, glucose, insulin, transferrin, selenium, ascorbic acid, a bioactive nanomaterial, and dexamethasone (SF3D). Additionally, a suitable medium can comprise at least one polysaccharide to be selected from the group consisting of: hyaluronic acid, chondroitin sulfate, dermatan sulfate, keratan sulfate, heparan, heparan sulfate, dextran, dextran sulfate, alginate, a bacterially-derived polysaccharide, a synthetic polysaccharide, a sulfated saccharide, and a non-sulfated saccharide. The polysaccharide can be in solution in the culture medium at a concentration of at least about 0.001% to about 10%.

Cartilage compositions according to the methods described herein can be prepared ex vivo by serial expansion and culture in vitro, and are surprisingly characterized by multiple layers of cells surrounded by a substantially continuous insoluble glycosaminoglycan and collagen-enriched hyaline extra-cellular matrix, enriched with high proteoglycan content, including aggrecan, as described for example in U.S. Pat. No. 6,645,764. A level of sulfated glycosaminoglycan S-GAG can be determined for example by an S-GAG assay and is indicative of the proteoglycan content.

Accordingly, the present disclosure encompasses cartilage compositions and methods as described herein.

B. Examples

The following examples are included to demonstrate the disclosure. It should be appreciated by those of skill in the art that the techniques disclosed in the following examples represent techniques discovered by the inventors to function well in the practice of the disclosure. Those of skill in the art should, however, in light of the present disclosure, appreciate that many changes could be made in the disclosure and still obtain a like or similar result without departing from the spirit and scope of the disclosure, therefore all matter set forth is to be interpreted as illustrative and not in a limiting sense.

Example 1: S-GAG Recovery of Neocartilage Implants

This study provides data demonstrating that, although the proteoglycan content of a neocartilage implant decreases during storage at temperature below physiologic temperature, the cells within the implant will revert back to matrix production when returned to 37° C./10% CO2. Neocartilage was otherwise prepared following methods and procedures described for example in U.S. Pat. Nos. 6,645,764; 6,235,316; 7,087,227; 7,273,756; and 8,017,394.

This report summarized data from a single lot of large (6.15 cm$^2$) neo cartilage seeded from E11-085 at 6.7×10$^6$ cells/implant:
1. Thawed and seeded on Day 1 under DIR-13-167.
2. Packaged in 65 mL PETG trays on or about Day 63.
3. Stored within the PETG trays at 22.5° C. and/or 30° C.
4. Removed from the trays on or about 60 days after packaging, i.e. Day 123 and returned to 37° C./10% CO$_2$ culture conditions in RM077 medium.
5. Harvested on or about Day 184 for testing (61 days in recovery culture).

The initial S-GAG content of the implants prior to storage on Day 1 was 1301 μg/cm$^2$, which met the current specification of not less than 500 μg/cm$^2$. After 61 days in recovery culture, the S-GAG content of all implants met or exceeded the pre-storage S-GAG content.

| Storage Condition | Post-Storage S-GAG content (μg/cm$^2$) | Post-Recovery culture S-GAG content (μg/cm$^2$) | % increase of S-GAG following recovery culture | % increase of S-GAG from initial harvest |
|---|---|---|---|---|
| Stored 57 days at 30° C. | 884 μg/cm2 | 1367 μg/cm2 | 55% | 5% |
| Stored 7 days at 30° C. and 50 days at 22.5° C. | 994 μg/cm2 | 2685 μg/cm2 | 170% | 106% |
| Stored 14 days at 30° C. and 44 days at 22.5° C. | 931 μg/cm2 | 2814 μg/cm2 | 202% | 116% |
| Stored 57 days at 22.5° C. | 1042 μg/cm2 | 2028 μg/cm2 | 95% | 56% |

The initial DNA content of the implants prior to storage on Day 63 was 26 μg/cm$^2$, which met the current specification of not less than 7 μg/cm$^2$.

| Storage Condition | Post-Storage DNA content (μg/cm$^2$) | Post-Recovery culture DNA content (μg/cm$^2$) | % increase of DNA following recovery culture | % increase of DNA from initial harvest |
|---|---|---|---|---|
| Stored 57 days at 30° C. | 30 μg/cm2 | 31 μg/cm2 | 3% | 19% |
| Stored 7 days at 30° C. and 50 days at 22.5° C. | 29 μg/cm2 | 30 μg/cm2 | 3% | 15% |
| Stored 14 days at 30° C. and 44 days at 22.5° C. | 29 μg/cm2 | 34 μg/cm2 | 17% | 31% |
| Stored 57 days at 22.5° C. | 26 μg/cm2 | 29 μg/cm2 | 12% | 12% |

As shown in FIG. 1, the proteoglycan content of all the implants increased by a minimum of 55% during the recovery culture period.

Although S-GAG is a necessary component of the implant for ease of handling, the decrease in this matrix component during storage does not appear to indicate a loss in the metabolic activity and/or viability of the implant.

Example 2: S-GAG Recovery of Neocartilage Implants

Although the proteoglycan content of the implant decreases during storage at temperature below physiologic temperature, the cells within the implant will revert back to matrix production when returned to 37° C./10% CO2. Neocartilage was otherwise prepared following methods and procedures described for example in U.S. Pat. Nos. 6,645,764; 6,235,316; 7,087,227; 7,273,756; and 8,017,394. A lot of small (24 mm) neocartilage was seeded from E13-001 at 4.9×10$^6$ cells/implant, and treated as follows:
1. Neocartilage thawed and seeded on Day 1.
2. Harvested at Day 62. Packaged in 65 mL of media in glass jars with silicone gaskets (primary container), and sealed inside a foil pouch (secondary container).
3. Stored for 57 days at 30° C.
4. Removed from packaging and returned to 37° C./10% CO2 culture conditions.
5. Maintained in culture for 64 days, and sampled for testing.

Following storage, the implants were maintained in a 37° C., humidified water-jacketed incubator (10% CO2) in Differentiation Media Complete (RM077 media supplemented with ascorbate and glutamine). Media was changed every 3-4 days (6 mL/implant).

Despite loss of S-GAG during storage, the cells within the implants surprisingly appear to remain viable and capable of producing matrix when returned to culture conditions.

| Phase Sample | S-GAG (μg/cm$^2$) | DNA (pg/cm$^2$) |
|---|---|---|
| Initial | 1683 | 23 |
| Post-Storage | 746 | (not measured) |
| Post-Recovery | 2136 | 24 |

The proteoglycan content of the implants nearly tripled during the recovery culture period and DNA remained essentially the same.

S-GAG is a necessary structural component of human cartilage the presence of which helps provide a hydrated, viscous gel that absorbs compressive load. However, the decrease in this matrix component during storage does not appear to indicate a loss in the properties of the implant.

Upon recovery culture, the levels of proteoglycan surpassed even pre-storage levels. This indicates that the cells remain viable and will continue producing aggrecan even after a period of storage.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. A cartilage replacement composition comprising:
neocartilage maintained at a temperature below physiologic temperature and comprising a reduced proteoglycan content relative to the proteoglycan content of the neocartilage at a physiological temperature, wherein the neocartilage is maintained at the temperature below the physiologic temperature for a period of time sufficient for the proteoglycan content of the neocartilage to decrease relative to the proteoglycan content of the neocartilage at a physiological temperature, wherein the storage period is at least about 1 week, wherein the temperature below physiologic temperature is about 30° C. or lower, and wherein the neocartilage at the temperature of about 30° C. or lower is capable of increasing the proteoglycan content when returned to a physiological temperature.

2. A cartilage replacement composition of claim 1 wherein the neocartilage is prepared ex vivo from isolated chondrocytes.

3. The cartilage replacement composition of claim 1, wherein the proteoglycan content comprises aggrecan content.

4. The cartilage replacement composition of claim 1, wherein the proteoglycan content comprises sulfated glycosaminoglycan (S-GAG) content.

5. The cartilage replacement composition of claim 1, wherein an initial proteoglycan content of the neocartilage at a physiological temperature before being maintained at about 30° C. or lower, comprises an initial S-GAG content of at least about 400 µg/cm2 or at least about 800 µg/cm2.

6. The cartilage replacement composition of claim 1, wherein an initial proteoglycan content of the neocartilage at a physiological temperature before being maintained at about 30° C. or lower, comprises an initial S-GAG content of from about 800 µg/cm2 to about 2500 µg/cm2.

7. The cartilage replacement composition of claim 4, wherein the composition is substantially free of type I, III and X collagen.

8. The cartilage replacement composition of claim 4, wherein the initial proteoglycan content of the composition indicates cartilage enriched in high molecular weight aggrecan.

9. The cartilage replacement composition of claim 8, wherein the high molecular weight aggrecan comprises at least about 80% of the initial proteoglycan content of the cartilage.

10. The cartilage replacement composition of claim 8, wherein the high molecular weight aggrecan comprises at least about 90% of the initial proteoglycan content of the cartilage.

11. The cartilage replacement composition of claim 1, wherein the composition comprises articular chondrocytes obtained from a human or animal donor.

12. The cartilage replacement composition of claim 7, wherein the composition comprises articular chondrocytes obtained from a cadaver.

13. The cartilage replacement composition of claim 8, wherein the composition comprises an implant.

14. The cartilage replacement composition of claim 1, wherein the composition is maintained at a temperature of about 20-30° C. and enclosed in a sealed container.

15. The cartilage replacement composition of claim 1, wherein the storage period is, at least about 2 weeks, at least about 30 days, at least about 50 days, or at least about 60 days.

16. The cartilage replacement composition of claim 1, wherein the composition is maintained in a serum-free medium.

* * * * *